US006028185A

United States Patent [19]
Ozias-Akins et al.

[11] Patent Number: 6,028,185
[45] Date of Patent: Feb. 22, 2000

[54] NUCLEIC ACID MARKERS FOR APOSPORY-SPECIFIC GENOMIC REGION

[75] Inventors: Peggy Ozias-Akins, Tifton; Wayne E. Hanna, Chula; Dominique Roche, Sycamore, all of Ga.

[73] Assignees: The United States of America as represented by the Secretary of Agriculture, Washington, D.C.; The University of Georgia Research Foundation, Inc., Athens, Ga.

[21] Appl. No.: 09/004,113

[22] Filed: Jan. 7, 1998

[51] Int. Cl.⁷ .................................................... C12N 15/11
[52] U.S. Cl. ........................ 536/23.6; 536/23.1; 800/266; 800/267
[58] Field of Search ................................. 536/23.6, 23.1; 800/266, 267; 435/172.1, 69.1, 6

[56] References Cited

U.S. PATENT DOCUMENTS

| | | | |
|---|---|---|---|
| 5,710,367 | 1/1998 | Kindiger et al. | 800/200 |
| 5,811,636 | 9/1998 | Hanna et al. | 800/200 |

FOREIGN PATENT DOCUMENTS

| | | | |
|---|---|---|---|
| 8802573 | 7/1988 | WIPO | A01H 1/00 |

OTHER PUBLICATIONS

Asker et al. Apomixis in Plants. CRC Press, Boca Raton, 1992.
Gustin et al. Apospory–linked molecular markers in buffelgrass. Crop Science. 37(3):947–951. (Abstract only), 1997.
Hart et al. Guidelines for nomenclature of biochemical/moleculer loci in wheat and related species. Proceedings of the Seventh International Wheat Genetics Symposium, held at Cambridge, UK, Jul. 13–19, 1988, pp. 1215–1218.
Welsh and McCelland, *Nucleic Acids Research*, vol. 18(24), pp. 7213–7218 (1990).
Williams et al., Nucleic Acids Research, vol. 18(22), pp. 6531–6535 (1990).
Harlan et al., *Botan. Gaz.,* vol. 125(1), pp. 41–46 (1964).
Duc et al., *C.R. Acad. Sc. Paris,* t. 292, Serie III, pp. 1227–1230 (1981).
Asker, S. *Hereditus,* vol. 91, pp. 231–240 (1979).
Scalla et al., *Plant Science Letters,* vol. 22, pp. 269–277 (1981).
Lefbvre et al, "Cytoplasmic Particles Associated with Male Sterility in Faba Bean (*Vicia faba*)", *Breeding and Genetics,* p. 10.
Asker, S., *Hereditus,* vol. 93, pp. 277–293 (1990).
Holl et al., "Genetic Transformation in Plants", *Genetic Transformation,* pp. 301–327.
Taliaferro, C., "Genetic control of Apomixis", pp. 44–47 Report of the 26th Southern Pasture and Forage Crop Improvement Conference Rio Piedras, Puerto Rico, May 7–9 (1969).
Petrov et al., "Transfer of some Elements of Apomixis from Tripsacum to Maize",*Apomixis and its role in Evolution and Breeding,* pp. 9–73, (1985).
Burton, G., *Crop Science,* vol. 29(2), pp. 252–255 (1989).
Fisk and Dandekur, *Scientia Horticulturae,* vol. 55, pp. 5–36 (1993).
Burton, G., *J. of Am. Soc. of Agron.,* vol. 40(10), pp. 908–915 (1948).
Dujardin and Hanna, *J. of Heredity,* vol. 74, pp. 277–279 (1983).
Gonzalez and Hanna, *J. of Heredity,* vol. 75, pp. 317–318 (1984).
Botstein et al., *Am. J. Hum. Genet.,* vol. 32, pp. 314–331 (1980).
Soller and Beckmann, *Theor. Appl. Genet.,* vol. 67, pp. 25–33 (1983).
Hanna et al., *J. of Heredity,* vol. 84(3), pp. 213–216 (1993).
Dujardin and Hanna, *Theor. Appl. Genet.,* vol. 69, pp. 97–100 (1984).
Dujardin and Hanna, *J. Genet. Breed.,* vol. 43, pp. 145–151 (1989).
Lubbers et al., *Theor. Appl. Genet.,* vol. 89, pp. 636–642 (1994).
Ozias–Atkins et al., *Theor. Appl. Genet.,* vol. 85, pp. 632–638 (1993).
Roche et al., Plant & Animal Genome V Conference, San Diego, CA, Jan. 12–16, 1997.

*Primary Examiner*—Lynette R F Smith
*Assistant Examiner*—Melissa L. Kimball
*Attorney, Agent, or Firm*—M. Howard Silverstein; John D. Fado; Gail E. Poulos

[57] ABSTRACT

The present invention is directed to nucleic acid markers for an apospory-specific genomic region from the genus Pennisetum. DNA for apomixis can be introduced into a plant using conventional methods of transfer or transformation in order to confer the apomictic trait to plants.

11 Claims, 2 Drawing Sheets

```
SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
          (A) LENGTH: 206 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Pennisetum squamulatum (vii) IMMEDIATE SOURCE:
           (B) CLONE: A10 5'end (xi) SEQUENCE DESCRIPTION: SEQ ID NO:1:

GTGATCGCAG ACATCAACCG CAGACAATCA ACCTACATGT TTAGGTAAAC CTTAATCATG      60

CAACCTCGGA ATATAAAAAT TTACAAGGAA AAACAATTGA CTGGTAACTA GTTTCATCAA     120

ACTAGCAGAG AAGTAGAACC TCAACCAATG TATAAACTAC ATATATGACT TTGAATTGAC     180

AGACTTAGCT GTATTTGGTA CACACC                                          206

(2) INFORMATION FOR SEQ ID NO:2:
```

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: A10 3'end (xi) SEQUENCE DESCRIPTION: SEQ ID NO:2:

ACCCTTTCTT GGCTTTATAA TACACTTTAA TACCTTCTAC CTGCAGGCTT CAGTGCTTCA      60

GGCATTGAGA TTCCTTAGAA ATAGGAACTT ACTTGTGCCC AGCCCAGAGG AGTAATTGGA    120

GCATCAAAGA AGGCGGGTGA CATGCATGCA CTGCGATCAC                          160

(2) INFORMATION FOR SEQ ID NO:3:

(i) SEQUENCE CHARACTERISTICS:
        (A) LENGTH: 259 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: A14

(xi) SEQUENCE DESCRIPTION: SEQ ID NO:3:

TNTNCTGGCA TGCAAATATA AGATGCTCTT ACATTGATTG AGTTTATTCC TATTTGGTCA      60

GACTGGAGCA ATTGGTTTTC TTTTTTAATT CAGAATATAT CCTTATTAGG TTCCCAATTA    120

CAAACGATTT TTATTTCCCT TTCTGTTTTA TGTCTTTGAG GTGGTTAGAG TTTGATGGTT    180

GGCTATAATC TATTTTTGAG TGACAGTGTG GTGCTAGACA CTACCCTCTC TGCACCAGTT    240

CTTCTTGTAC CAGCACAGA                                                 259

(2) INFORMATION FOR SEQ ID NO:4:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:

(B) CLONE: C4

(xi) SEQUENCE DESCRIPTION: SEQ ID NO:4:

CCGCATCTAC AATAATCAAA AGAAGAGACA GGGATTACTC TTTCCAATGT CCTGAAGTCT      60

TTATTGTTCC TCTTCATTGG TTCTTTCCTT TAATTTCTCC TTTGTCATCA TTTGAACACT     120

AGTGCAGCAT GTAGCATATC ATTGGTGACC CGCTGGCATG CCTATGCAGC AATATTGCCA     180

GTGACATCCA AGCGGGTGAG GTTGTTCATG AGCTTCAACA TTTATTTTGC CTTGAATGCT     240

CAAAAACTAT TTTGTGTTCT CTGGACCCAA GAAGGATATA CGCTACAATT TCTTTCTTGA     300

GACTGCTAAA ATATCCTCAA GAGGGAGCTG GTAATTAAGC CATGGCTCGG TCATAAGTTC     360

CTGATGTCTC ACAAACCTAC CATTAAGTGG ACCACAATTC ATTGATGTGT AGGCACTCCG     420

TCACTTCCAA ATTCTTATAT ATCTTGTTTT CCCAGTGCCT TTATTTCAGC ACAGTTGAAT     480

AAGCCTTTGG TTCATTGCCA CAAAATAGTT CGGGTAGATG CGG                      523

(2) INFORMATION FOR SEQ ID NO:5:

(i) SEQUENCE CHARACTERISTICS:
        (A) LENGTH: 274 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: O7 5'end (xi) SEQUENCE DESCRIPTION: SEQ ID NO:5:

CAGCACTGAC ATCAACTAGG ACGATGAAAT TAAGTGTGTA AAAAGGTCAG TAATAAGAGC      60

CAGTGCAAAA GCATTGCAAA CCTTGAGATG GTATTTCTTC TAAAGATTTT CACGGGGATT    120

GGAGAGGCAG GTACCAGATA TAATAATCCA ACAAGACAGT AGCCCTTCAC CAATCAGGTA    180

TGATAAGTGT GGGTCAAGAA CACCATTCAG TACCCAGTCA GTGTTAGGAT AGCCAGTGCA    240

GTGCACCCAC ACAACAGCAT GGAGGCCACG TTTC                                274

(2) INFORMATION FOR SEQ ID NO:6:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: O7 3'end (xi) SEQUENCE DESCRIPTION: SEQ ID NO:6:

CACAACAGAC ACTCAAATCA TTTAGCTAAT AATTCAATAT ATAGAACAGC AGAGATGTAA      60

```
GGATACAAAA TGGTCAACAT TAGAGCAACT AACAACAGCA GATATTGTCA GTACGTACTA        120

CTCAGCTAGT TAGCTAGGAT TCAGTAAAGT TGGTCAGTGC T                           161

(2) INFORMATION FOR SEQ ID NO:7:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: P16 5'end (xi) SEQUENCE DESCRIPTION: SEQ ID NO:7:

CCAAGCTGCC ATATCTCCAT GCTCAACACT AACAAAACCA TATTTGTCCC TGCTCACAGC         60

TCTCCCATTG ACGACCCATC ATTTTATCTC GTTTCTTTCC TTTGCCAAGG ATTTTTCAGT        120

CAATTTGGGT AACTCCTTGA TAGTTCTGAT GTCC                                   154

(2) INFORMATION FOR SEQ ID NO:8:

(i) SEQUENCE CHARACTERISTICS:
        (A) LENGTH: 263 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: P16 3'end (xi) SEQUENCE DESCRIPTION: SEQ ID NO:8:

ACTATGCATA AGTTCTCATC AGCTGAGAAA CTACTGACCA GCACAACTGA CCCAGCCAAG         60

CAGGTTCTCA TGCAATAACA CTGACCAAAC AAGCCTGAAT GTAACAAGTT TCAAGTTTCT        120

GGCTACAATG AACTCACAAT GCATCTCCCT TTAGGTTGCT ATAGAACTTG CCTTTTGGGT        180

TGAGGGTCTC CTTAAGAATG AAATCGCACA GCATGTCCCG GATCGGCTTT AGTTCTTCTT        240

TAGTAACCTT TTGGGCAGCT TGG                                               263

(2) INFORMATION FOR SEQ ID NO:9:

(i) SEQUENCE CHARACTERISTICS:
        (A) LENGTH: 199 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (vi) ORIGINAL SOURCE:
            (A) ORGANISM: Pennisetum squamulatum (vii) IMMEDIATE SOURCE:
            (B) CLONE: Q8 5'end (xi) SEQUENCE DESCRIPTION: SEQ ID NO:9:

ATACAGCGGA TCGAGCTTGC CAATCGGGAA ATCCATCGAA CCTCCCAAGA AGTCGCCATC        60

ACCCATTCAC TGTCGCTGCC GTGAAGGAGA CGGAGGACGG ACAAACAGAG GAGTGCGACG        120

GCCGACGAGG AAGGAGGATT TGGCTTTCTG CGGGAGTGTT TTGCAGGCTC TGCAGGCCGT        180

GTGCAGGCTC GCAGGCTTG                                                    199

(2) INFORMATION FOR SEQ ID NO:10:

(i) SEQUENCE CHARACTERISTICS:
            (A) LENGTH: 213 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Pennisetum squamulatum (vii) IMMEDIATE SOURCE:
            (B) CLONE: Q8 3'end (xi) SEQUENCE DESCRIPTION: SEQ ID NO:10:

TCATCATTAG AAAAAGTTCA TGCTCTGAGA TACTCCAACA ACTAAATATT GCCGTAGATT        60

ATTCATTGAG AAAAAGGTGA GTCATGCAAT GAGAAAATTG ATATATTGAT GGACCAGAAC       120

CTCTCAACAT TTAAGTGATT TTTTGGGAAC GCATTGTGTT AATTAATGCA TTAAAAGAAT      180

TGTAGTCCAA AAGATCCATC ACCATCCGCT GGA                                   213

(2) INFORMATION FOR SEQ ID NO:11:

(i) SEQUENCE CHARACTERISTICS:
            (A) LENGTH: 625 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Pennisetum squamulatum (vii) IMMEDIATE SOURCE:
            (B) CLONE: R13

(xi) SEQUENCE DESCRIPTION: SEQ ID NO:11:

GGACGACAAG AACAAGAAGG ACGACTCAGA TTCTGACTCT GAGCGTGAGG TGGGAGGCTT       60

GGAAAATTCT TGGTTGATCG ACTCCAGTTG TTCGAGGCAC ATGACCGGAG ATAGGAGGTG      120

GTTCTCCAGC CTCACCCCAG TGGTGTCAAG GGAGTACATC ACTTTCGGGG ATAATGGTAA      180

```
AGGTAGAGTG CTGTCTGAGG GTGCTATTCA GGTGAGCGAC AGCTTTACTC TCAAATGTGT        240

GGCTCTTGTC AAGAATCTTG GATTCAATTT TCTTTCAGNT TCCCCAGGTT GCTTGGAGAG        300

GGTCTTGGAN GGTCNGTTTT AAAGAGTGGG GGTTTCTTCG CATTCCTGAT TCTCGGGGGG        360

AACTTGGGTG TGNGAATCTT CCCCNAAGGG ANAAGTNTTT TCCGGGCNGN TTTTNNCTTA        420

AACAATTGGG CCCGNTCCGN GGCTTGGTGG TTGGNNCCCC CGANTTAACT TTGGGGGGGG        480

GAATGGAGAT TGGGCCAATT GGGNCNTTGG GTTTCTCNAC TCCTTGGGNN NTCAANAACC        540

TATTTTNNGG TTGNCCNANN CAAATTCCNN AAGGGTTTGG GTTGGGNGCC CTGGNNGCCC        600

ATCAATTNGG GGGGCCCCNN AAGGG                                             625

(2) INFORMATION FOR SEQ ID NO:12:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: U12 5'end (xi) SEQUENCE DESCRIPTION: SEQ ID NO:12:

TCACCAGCCA GTTCAACCCA AAAGCAAGCT AGATGAGGAA AGGTGGACAA TTCACTTATA         60

CTCCAACAAG AAGGACCAGA CAGCTAGCTT TTTTGCGCCA ACTTAAAGAA ATAATCTAGA        120

AGAGACAATA CCAAAAAGGC AACTAAACCA TTGTAGCATT ACCATAGAAA TAATTATTAA        180

TGGTTCAAAG GCTAGAAATA ATTAACTCAC                                        210

(2) INFORMATION FOR SEQ ID NO:13:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: U12 3'end (xi) SEQUENCE DESCRIPTION: SEQ ID NO:13:

AATAACGAAA CTCTCAGTGA CTGTGTGTAC AATTAGTTGC ATGACCGAAA TAAATCCCAA         60

TAGGCATTGC TGAAGCTTTT TTTGTCAATT GAATTTTTTT CAAAAATACC AACAACCAAA        120

ATCTTTTGAT CTTCTGGTGA TGGTATGTAA ACAATCCTGC AGGTTCATGA TGGCTGGTGA        180

(2) INFORMATION FOR SEQ ID NO:14:
```

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: V4 5'end (xi) SEQUENCE DESCRIPTION: SEQ ID NO:14:

```
CCCTCACGAA CTACTTCACA TCCATTTTCT CTTCCAGTCA GCTGAATTCA GCAACAATCC       60

CCACCCCTAT CAATCCAAAT GTCCCTGAAT TCCAATCGCC TACTTCTCAG AATGTCCCTG      120

AGCAACTACC ACACCAAGAT CAAGATCCCC TCCTAGCTTC TATATTCAGG TACACATATT      180

CAACACCTCT CTTAATG                                                     197
```

(2) INFORMATION FOR SEQ ID NO:15:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: V4 3'end (xi) SEQUENCE DESCRIPTION: SEQ ID NO:15:

```
CAACTCTCTC TAAAGGTCCT AGGCATAGAG CGACATATGA GTTAGTTCTA GGTTCTAATG       60

TACTATACAC ACAAAGTTAG TCGGAACAAG TTAGACACAC TTAGTATTGA TGAACATTGA      120

CTTAAGCACT GAGGCACAAA CAGGGAGCTA CCCTCNCGCG TCGCTTTTGC ACGTCTCCGG      180

TTTGTAGATT TTAGACTCCT ACAGCTTATC CGATCGTGAG GGG                        223
```

(2) INFORMATION FOR SEQ ID NO:16:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: W10 5'end (xi) SEQUENCE DESCRIPTION: SEQ ID NO:16:

```
TCTTTTTAAT TCTTGCAATT CAGATTTTGT TAACATGTAT TTCTCTGTCG TACTTGGTCC        60
AAATTTAATG ATTTTTTCTA AATTTTTATA AATCTCCATC TTTTTATTGA TTTCATTTTC       120
TAGTGTATAT TCTATTCTGA TATGTTATAA GCTATCTGTC TTGT                        164
```

(2) INFORMATION FOR SEQ ID NO:17:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: W10 3'end (xi) SEQUENCE DESCRIPTION: SEQ ID NO:17:

```
ATTACAAGTT TAAGTACCAA ATTATGTTGA CAATTCAATT TCTAGAATTT TAGAGCACAT        60
TAATTATTAT TAGAATTATT ATATCATGAG CATGAGATGT AAAATCGAAT CATAAGAATT       120
TTGAGTACAC AAGTGTGACT GTTGATAATT TATTCAAATA CTAAATGCCC AAGAAAGAAT       180
TGATGTTATT TTTAATGATT TTTTAGGAGC TGTTTTATGG GCTCTAATAT TTGAGGGATG       240
C                                                                       241
```

(2) INFORMATION FOR SEQ ID NO:18:

(i) SEQUENCE CHARACTERISTICS:
        (A) LENGTH: 217 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pennisetum squamulatum (vii) IMMEDIATE SOURCE:
        (B) CLONE: X18 5'end (xi) SEQUENCE DESCRIPTION: SEQ ID NO:18:

```
GGTGGCGAAG TTGGGAAGAA AGCCGAGTTG TTTGAGAAGA AATTTTTATC GGCTCCCATT        60
CACACCCCCT CTCTGGGCGC CGTTTTGATC CTTCACTTGG CTCTAGTATT GCAGGTGTAG       120
AATGCGGCTT GTTCGCATTG CTGTGGTGAA GAACAGCACG AAAGCTAGCA TGCGCTTAGA       180
GTGAGAGGCA GTAGCTGTCA GCTGTGCTAT GTCAGTG                                217
```

(2) INFORMATION FOR SEQ ID NO:19:

(i) SEQUENCE CHARACTERISTICS:
        (A) LENGTH: 226 base pairs
        (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Pennisetum squamulatum (vii) IMMEDIATE SOURCE:
            (B) CLONE: X18 3'end (xi) SEQUENCE DESCRIPTION: SEQ ID NO:19:

ACTGGGTACA CGCGCTGTGA TCACAGGTAG CTTGCGTCAG AGGAAGCAAG GCTGCGGTGG      60

ATGCGTATCC ACTCGATGGG AATTTTCGAC GCACTTCCAA GATTGCCCTG AGGGGTATGT     120

ATCTATAGTT AAGTGTAGAA GGGTAGTATG GTCATTTCTC ACCCCGGCAG GACCCGATAT     180

ATAGACTAGA TTTGTAGAGA TGGCAGCCAT CCTTTGCCAC CTAGTC                    226

(2) INFORMATION FOR SEQ ID NO:20:

(i) SEQUENCE CHARACTERISTICS:
            (A) LENGTH: 537 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Pennisetum squamulatum (vii) IMMEDIATE SOURCE:
            (B) CLONE: ugt 197/71W (xi) SEQUENCE DESCRIPTION: SEQ ID NO:20:

ACTCNCCATC TGTCGNTCGT NGNCTGTCCC CCCCCTCCCC CACCAGGAAA AAGGGGGATN      60

TACTAAACNT CGNNNTATGG AGTCGANGAA ANNCAAGTTC CTCNCGGAGC TCTTTCAGNT     120

CGCGTCGACT CCGTCGANCG TAGCCGTCGC NCCNCCCCCT CCTCCTNCTG CAGACCTCCA     180

AACAGCACGT CCTCGAGCGC GGCGCGGAGG CCCACCGCGA TGGAACCTCG TCTGTGGAAG     240

CAACGGCGGT AGTGATAACT GCCAGCGGCT TATTTTATTT GTTTCAACAG TCCATGGTTC     300

ACATGCTGCA GACCGNTCGC ATTTTGCCTC TGACAACGAC GGTGCGGCTG CCACTATGGT     360

TATGGTTCAG TACAACCGAA CCATACTCTC CCTCGGTTCG TCCACGGCGG GTGCTCGCAT     420

CACATCACAA CGGATGAATA AAACGGTGTT GGGAGANTNG GTGCTACTCG ATCATGACTT     480

GCTTGGGCAG AACGCATCCG NGTGCTTTAC ATAACCGGAC AAGTTAACTT TTACCGC        537

(2) INFORMATION FOR SEQ ID NO:21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO

```
    (iv) ANTI-SENSE: NO (vii) IMMEDIATE SOURCE:
        (B) CLONE: A10H primer 1

(xi) SEQUENCE DESCRIPTION: SEQ ID NO:21:

AAACCTTAAT CATGCAACCT CGGA                                              24

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: A10H primer 2

(xi) SEQUENCE DESCRIPTION: SEQ ID NO:22:

ATGTCACCCG CCTTCTTTGA TGCT                                              24

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: A14M primer 1

(xi) SEQUENCE DESCRIPTION: SEQ ID NO:23:

TTGATTGAGT TTATTCCTAT TTGG                                              24

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: A14M Primer 2

(xi) SEQUENCE DESCRIPTION: SEQ ID NO:24:

GTGCTGGTAC AAGAAGAACT GGTG                                              24

(2) INFORMATION FOR SEQ ID NO:25:

(i) SEQUENCE CHARACTERISTICS:
```

```
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: C4 Primer 1

(xi) SEQUENCE DESCRIPTION: SEQ ID NO:25:

CCGCATCTAC AATAATCA                                                18

(2) INFORMATION FOR SEQ ID NO:26:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (A) LIBRARY: C4 Primer 2

(xi) SEQUENCE DESCRIPTION: SEQ ID NO:26:

GAAATAAAGG CACTGGGA                                                18

(2) INFORMATION FOR SEQ ID NO:27:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: O7M Primer 1

(xi) SEQUENCE DESCRIPTION: SEQ ID NO:27:

CAGCACTGAC ATCAACTAGG ACGA                                         24

(2) INFORMATION FOR SEQ ID NO:28:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: O7M Primer 2
```

(xi) SEQUENCE DESCRIPTION: SEQ ID NO:28:

AGCACTGACC AACTTTACTG AATC                                               24

(2) INFORMATION FOR SEQ ID NO:29:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: P16R Primer 1

(xi) SEQUENCE DESCRIPTION: SEQ ID NO:29:

CCAAGCTGCC ATATCTCCAT GCTC                                               24

(2) INFORMATION FOR SEQ ID NO:30:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: P16R Primer 2

(xi) SEQUENCE DESCRIPTION: SEQ ID NO:30:

ATCCGGGACA TGCTGTGCGA TTTC                                               24

(2) INFORMATION FOR SEQ ID NO:31:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: Q8M Primer 1

(xi) SEQUENCE DESCRIPTION: SEQ ID NO:31:

GAGCTTGNCC AATCGGGAAA                                                    20

(2) INFORMATION FOR SEQ ID NO:32:

(i) SEQUENCE CHARACTERISTICS:
           (A) LENGTH: 21 base pairs
           (B) TYPE: nucleic acid
           (C) STRANDEDNESS: single
           (D) TOPOLOGY: linear

```
        (ii) MOLECULE TYPE: DNA (genomic)

(iii) HYPOTHETICAL: NO (iv) ANTI-SENSE: NO (vii) IMMEDIATE SOURCE:
              (B) CLONE: Q8M Primer 2

(xi) SEQUENCE DESCRIPTION: SEQ ID NO:32:

ATGGTGATGG ATCTTTTGGA C                                              21

(2) INFORMATION FOR SEQ ID NO:33:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: R13 Primer 1

(xi) SEQUENCE DESCRIPTION: SEQ ID NO:33:

GGACGACAAG AACAAGAAGG ACGA                                           24

(2) INFORMATION FOR SEQ ID NO:34:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: R13 Primer 2

(xi) SEQUENCE DESCRIPTION: SEQ ID NO:34:

GAATAGCACC CTCAGACAGC ACTC                                           24

(2) INFORMATION FOR SEQ ID NO:35:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: U12H Primer 1

(xi) SEQUENCE DESCRIPTION: SEQ ID NO:35:

TCACCAGCCA GTTCAACCC                                                 19
```

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: U12H Primer 2

(xi) SEQUENCE DESCRIPTION: SEQ ID NO:36:

ATTGTTTACA TACCATCACC AGAA        24

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: V4 Primer 1

(xi) SEQUENCE DESCRIPTION: SEQ ID NO:37:

TCGGATAAGC TGTAGGAGTC T        21

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: V4 Primer 2

(xi) SEQUENCE DESCRIPTION: SEQ ID NO:38:

CACATCCATT NTCTCTTCCA G        21

(2) INFORMATION FOR SEQ ID NO:39:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: W10M Primer 1

(xi) SEQUENCE DESCRIPTION: SEQ ID NO:39:

CATGTATTTC TCTGTCGTAC TTGGTC                                              26

(2) INFORMATION FOR SEQ ID NO:40:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: W10M Primer 2

(xi) SEQUENCE DESCRIPTION: SEQ ID NO:40:

AGCCCATAAA ACAGCTCCTA AA                                                  22

(2) INFORMATION FOR SEQ ID NO:41:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: X18R Primer 1

(xi) SEQUENCE DESCRIPTION: SEQ ID NO:41:

AGTTGGGAAG AAAGCCGAGT TGTT                                                24

(2) INFORMATION FOR SEQ ID NO:42:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: X18R Primer 2

(xi) SEQUENCE DESCRIPTION: SEQ ID NO:42:

CAATCTTGGA AGTGCGTCGA AAAT                                                24

(2) INFORMATION FOR SEQ ID NO:43:

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: ugt197-71W Primer 1

(xi) SEQUENCE DESCRIPTION: SEQ ID NO:43:

GGATGAATAA AACGGTGTTG GGAG                                              24

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: ugt197-71W Primer 2

(xi) SEQUENCE DESCRIPTION: SEQ ID NO:44:

AGAACAACCG CACAAGTGAG AGAA                                              24
```

NUCLEIC ACID MARKERS FOR APOSPORY-SPECIFIC GENOMIC REGION

BACKGROUND OF THE INVENTION

1. Field of the Invention

This invention relates to nucleic acid markers for a locus that controls apomixis and vectors containing the DNA. The markers are also useful for marker-assisted selection in conventional crossing programs.

2. Description of the Related Art

Reproduction in plants is ordinarily classified as sexual or asexual. The term apomixis is generally accepted as the replacement of sexual reproduction by various forms of asexual reproduction (Rieger et al, IN Glossary of Genetics and Cytogenetics, Springer-Verlag, New York, N.Y., 1976). Apomixis is a genetically controlled method of reproduction in plants where the embryo is formed without union of an egg and a sperm. There are three basic types of apomictic reproduction: 1) apospory-embryo develops from a chromosomally unreduced egg in an embryo sac derived from the nucellus, 2) diplospory- embryo develops from an unreduced egg in an embryo sac derived from the megaspore mother cell, and 3) adventitious embryony- embryo develops directly from a somatic cell. In most forms of apomixis, pseudogamy or fertilization of the polar nuclei to produce endosperm is necessary for seed viability. These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progenies of specially adapted or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. Apomixis can make hybrid development more efficient. It also simplifies hybrid production and increases genetic diversity in plant species without good male sterility systems.

In sexual reproduction, usually a megaspore mother cell arising from the hypodermal layer of the ovule enlarges and goes through meiosis to form a linear tetrad of megaspores each with a haploid chromosome number. The three micropylar spores degenerate while the functional chalazal spore enlarges to form an embryo sac with an egg, two polar nuclei, two synergids, and three antipodals.

In apospory, a megaspore mother cell may begin enlarging and even produce chromosomally reduced megaspores but this sexual tissue usually degenerates before embryo sac development. Instead, somatic cells of the nucellus enlarge and the nuclei of these cells go through mitotic divisions to form one to many embryo sacs per ovule each with one to eight chromosomally unreduced nuclei. Aposporous apomicts are characterized by the participation of one or more nucellar cells in the direct formation of one or more embryo sacs. Each nucleus of the aposporous embryo sac has the somatic chromosome number and genotype of the maternal plant. Some aposporous species, pseudogamous apomicts, require pollination and fertilization of polar nuclei for the development of endosperm, but the unreduced aposporous egg develops without fertilization (parthenogenetically). Female meiosis usually is disturbed in aposporous apomicts that form all of their seed asexually (obligate apomicts) so that no functional megaspore continues development beyond the first mitotic division. Facultative apomicts exist in which meiosis and aposporous development occur simultaneously and both reduced and unreduced embryo sacs ultimately reside in the same individual and/or the same ovule. Thus, the two modes of reproduction, sexual and asexual, can coexist or one can be dominant over the other. During obligate apospory, several events must be coordinately regulated, i.e., disturbance or failure of meiosis, aposporous embryo sac development, parthenogenesis; nevertheless only one or a few genes may be responsible for the cascade of events. Some genetic studies suggest that aposporous apomixis is simply inherited (Asker et al, Apomixis in Plants, CRC Press, 1992; Nogler, Embryology of Angiosperms, B. M. Johri, Ed., Springer-Verlag, 475–518, 1984; Winkler, Progr. Rei. Bot., Vol. 2, 293, 1908).

The main difference in diplospory compared to sexual development is that a single megaspore is derived from the megaspore mother cell without meiosis, thus this megaspore has the somatic chromosome number. An embryo sac similar in appearance to a sexual embryo sac develops, but with an egg containing the somatic chromosome number.

In adventitious embryony, embryos develop directly from somatic cells of the ovule without formation of embryo sacs. Sexual sacs which are needed for endosperm formation may also form in the same ovule.

Introducing the apomictic trait into normally sexual crops has been attempted. Asker (Heredias, Vol. 91, 231–240, 1979) reports that attempts have been unsuccessful with wheat, sugar beets, and maize. PCT publication WO 89/00810 (Maxon et al, 1989) discloses inducing an apomictic form of reproduction in cultivated plants using extracts from nondomesticated sterile alfalfa plants. The PCT discloses that a soybean hybrid was produced applying this extract to the soybean which was male sterile through the $F_4$ generation. The publication further discloses that corn treated with the extract displayed a sterility conversion of 15–26% for seven of the eight genotypes treated. When induction of male sterility was evaluated in sorghum, sunflower, pearl millet, and tomato it was reported that there was reduced seed set in sorghum, pearl millet, and sunflower and reduced fruit set in tomato.

It would be ideal to find genes controlling obligate or a high level of apomixis in the cultivated species and be able to readily hybridize cross-compatible sexual x apomictic genotypes to produce true-breeding $F_1$ hybrids. In reality, most desirable genes controlling apomixis are found in the wild species which are distantly related to the cultivated species. Although interspecific crosses may be possible between the cultivated and wild species, chromosome pairing between genomes is usually low or nonexistent.

Although apomixis is effectively used in Citrus to produce uniform and disease- and virus-free rootstock (Parlevliet JE et al, in Citrus. Proc. Am. Soc. Hort. Sci., Vol. 74, 252–260, 1959) and in buffelgrass (Bashaw, Crop Science, Vol. 20, 112, 1980) and Poa (Pepin et al, Crop Science, Vol. 11, 445–448, 1971) to produce improved cultivars, it has not been successfully transferred to a cultivated crop plant. The transfer of apomixis to important crops would make possible development of true-breeding hybrids and commercial production of hybrids without a need for cytoplasmic-nuclear or chemically-induced male sterility and high cost, labor-intensive production processes. An obligately apomictic $F_1$ hybrid would breed true through the seed indefinitely and could be considered a vegetative or clonal method of reproduction through the seed. The development of apomictically reproducing cultivated crops would also provide a major contribution toward the food security in developing nations (Wilson et al, IN Proceedings of the International Workshop on Apomixis in Rice, Changsha, People's Republic of China, Jan. 13–15, 1992. Hunan Hybrid Rice Research Center, Changsha, People's Republic of China)

Genes involved in apomictic reproduction have not been cloned to date. Therefore, nucleic acid markers tightly linked to the apomixis trait are useful for obtaining the gene(s) which are involved in apomictic reproduction. These markers are also useful for identifying cultivated hybrid plants having apomictic reproduction. The present invention, described below, provides markers which are tightly linked to the apomictic trait which are different from the related art.

SUMMARY OF THE INVENTION

It is, therefore, an object of the present invention to provide novel nucleic acid markers for an apospory-specific genomic region.

Another object of the present invention is to provide novel nucleic acid markers which strictly cosegregate with aposporous embryo sac development clearly defining a contiguous apospory-specific genomic region (ASGR).

A still further object of the present invention is to provide novel nucleic acid markers which identify a contiguous apospory-specific genomic region in which no genetic recombination is detected.

Another object of the present invention is to provide novel nucleic acid markers which recognize unique restriction fragments, by DNA-DNA hybridization, associated with apomixis.

Another object of the present invention is to provide novel nucleic acid sequences for marker-assisted selection of apomictic plants produced in conventional crossing programs.

Another object of the present invention is to provide primers for obtaining the nucleic acid markers of the present invention.

A still further object of the present invention is to provide a contiguous apospory-specific genomic region which is linked with the nucleic acid markers of the present invention.

A still further object of the present invention is to provide a method for marker-assisted selection of apomictic plants using novel nucleic acid markers for a contiguous apospory-specific genomic region.

Further objects and advantages of the invention will become apparent from the following description.

DEPOSIT OF MICROORGANISMS

E. coli containing the rDNAs (recombinant DNAs) of the present invention as plasmids have been deposited in accordance with the provisions of the Budapest Treaty with the American Type Culture Collection, 12301 Parklawn Drive, Rockville, Md. 20852 on Dec. 4, 1997. The Accession Numbers are 98601, 98602, 98603, 98604, 98605, 98606, 98607, 98608, 98609, 98610, 98611 and 98612 which correspond respectively to 07M, A10H, V4, UGT197-71W, Q8M, C4, X18R, P16R, R13, A14M, U12H and W10M.

DETAILED DESCRIPTION THE INVENTION

Figure 1:
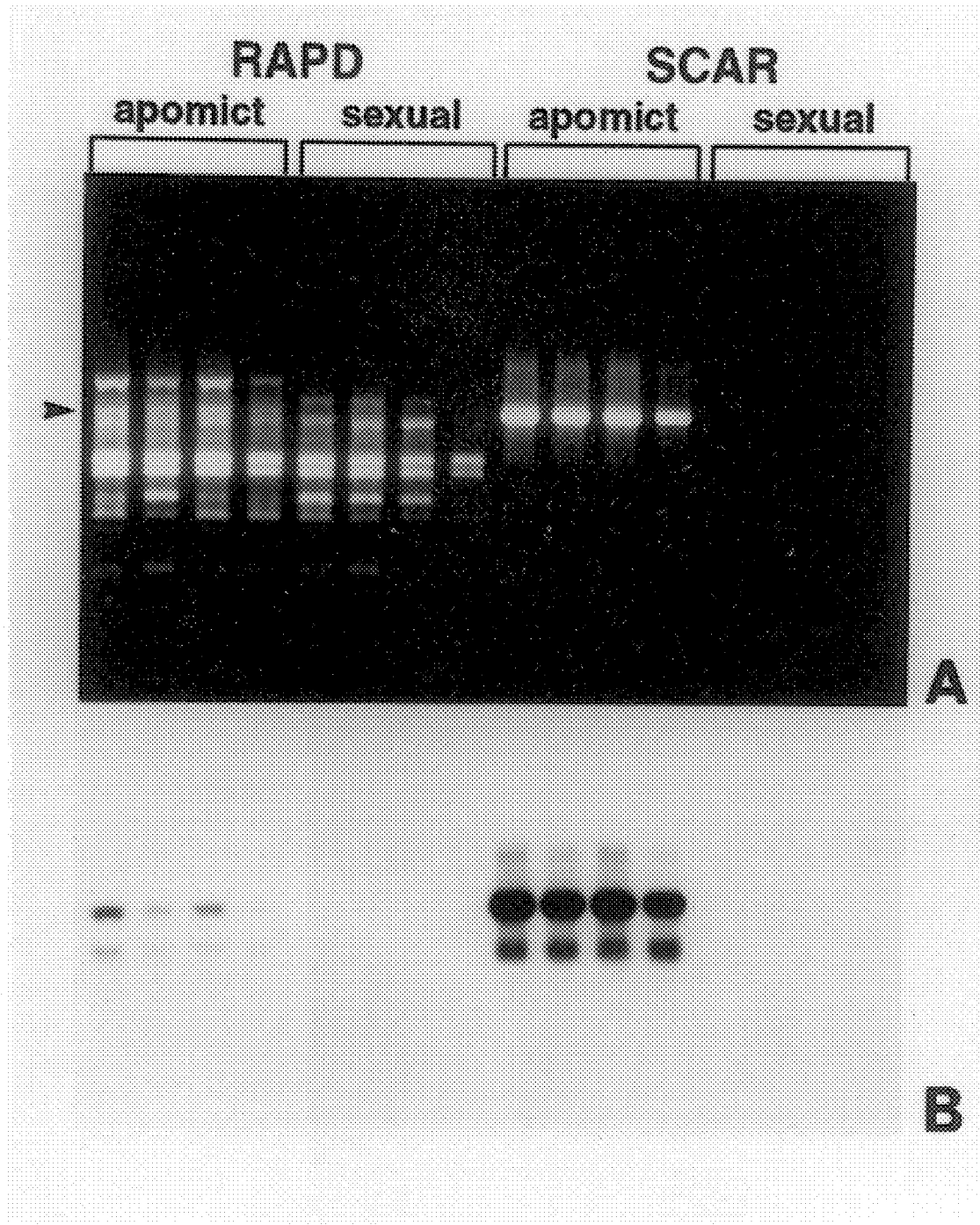
FIG. 1A shows the RAPD pattern with operon primer P16 (first group of lanes labeled A and S) and SCAR pattern (second group of lanes labeled A and S). Each lane represents four genotypes bulked by phenotype (A=apomictic, S=sexual).
FIG. 1B shows blot of a gel shown in A probed with the cloned P16 RAPD fragment.

Apomixis is a naturally occurring mode of reproduction that results in embryo formation without the involvement of meiosis or fertilization of the egg. Seed-derived progeny of an apomictic plant are genetically identical to the maternal parent. A form of apomixis called apospory occurs in the genus Pennisetum, a taxon in the grass family. A cultivated member of this genus, pearl millet (*P. glaucum*), reproduces sexually. A wild relative of pearl millet, *P. squamulatum*, which is an obligate aposporous species, is cross compatible with pearl millet when used as a pollen donor in an interspecific cross.

Although much is published on genetic analysis of apomicts that presents evidence for recessive and dominant control, single and multiple gene action (Asker et al., Apomixis in Plants, CRC Press, 1992), the most recent data on well characterized apomicts within the grass family, *Tripsacum dactyloides, Cenchrus ciliaris* (*Pennisetum ciliare*) and *P. squamulatum*, strongly support dominant inheritance of a single locus trait. All of these species are polyploid (tetraploid or hexaploid), thus either disomic or polysomic inheritance could be functioning. None of these species displayed strict bivalent pairing of chromosomes at melosis (Arnand et al., Cytologia, volume 29, 324–329, 1964; Hignight et al., Link. Bot. Gaz., volume 152, 214–218, 1991; Dujardin et al., Theor. Appl. Genet., volume 67, 197–201, 1984), but the extent of homologous or homeologous pairing of chromosomes bearing the apomixis locus is not known. A common segregation pattern for all three species, however, was often a ratio less than the predicted 1 apomict : 1 sexual (*T. dactyloides*, Leblanc et al., Theor. Appl. Genet., volume 90, 1198–1203, 1995; *C. ciliaris*, Sherwood et al, Crop Sci., volume 34, 1490–1494, 1994).

A contiguous block of non-recombinant DNA, an Apospory-Specific Genomic Region (ASGR), encoding for apomixis, is delineated by the nucleic acid markers (Table 2 and SEQ ID NO 25–36) of the present invention in interspecific crosses of *Pennisetum glaucum*, pearl millet; and *Pennisetum squamulatum*, a wild relative of pearl millet. Primers for these markers are presented in Table 1 and are SEQ ID 21–44. SEQ ID 1–20 represent partial 3' and 5' end sequences of the markers. These sequences strictly cosegregate with aposporous embryo sac development clearly defining the contiguous ASGR. Four of these markers, UGT 197-71W (ATCC 98604), C4-500 (ATCC 98606), Q8-800 (ATCC 98605) and A14-200 (ATCC 98610), also hybridize to hemizygous regions in the *Pennisetum squamulatum* genome. Four markers, A14, C4, Q8 and ugt 197-71W are unique to the ASGR and have no homology to unlinked sequences anywhere else in *P. squamulatum* or *P. glaucum* genomes as judged by DNA-DNA hybridization. Three of these, A14, Q8 and ugt 197-71W are linked within a physical distance of about 60 kb. Sequences A10 (ATCC 98602), 07 (ATCC 98601), R13 (ATCC 98609) and U12 (ATCC 98611) also recognize unique restriction fragments, by DNA-DNA hybridization, associated with apomixis. The remaining seqeunces P16 (ATCC 98608), V4 (ATCC 98603), W10

(ATCC 98612) and X18 (ATCC 98607), hybridize with dispersed repetitive DNA in both apomictic and sexual genotypes but the sequence-characterized amplified regions are contained within the ASGR. The lack of recombination within the ASGR suggests (a) more than one gene in a cluster of genes may be operating to confer apomictic reproduction or (b) that a novel genetic mechanism contrary to the dogma of one gene-one protein may be functioning. An ASGR has not been discovered or postulated in any other apomictic species.

Presently, several methods exist for identifying, characterizing and isolating a gene from a plant genome. Each rely on the use of nucleic acid markers and their close association or linkage to the locus of interest. Markers close to the gene are considered tightly linked to the gene and are of most value. Other markers associated with the gene, but not necessarily tightly linked to it, are also of use but of less immediate value. The markers described in Example 2 range in size from about 200–1600 bp and are tightly linked with the ASGR of the present invention. These markers provide an ideal system for following the apomictic trait.

The bands generated in a RAPD assay can be isolated from the agarose gel and cloned into a plasmid cloning vector, or any other suitable vector. These clones can be used as markers for identifying the presence or absence of apomixis in a Pennisetum species or hybrid.

Since no genes known to be involved in apomictic reproduction have yet been cloned, the only evidence at the present time for a complex locus on a single linkage group is the present invention finding that the nucleic acid markers of the present invention found linked to the trait do not recombine with it or between each other. It is remote that false or pseudo-linkage would have resulted in such an extreme pattern of non-recombination in a population of 397 individuals as well as a high ratio of apomictic to sexual individuals. During chromosomal reassortment, the probability of joint segregation, $P(j.s)$, of n subsets of markers with either disomic or tetrasomic inheritance is given by the following formula, $P(j.s)-0.5^n$ Thus the probability of independent segregation, $P(i.s)=-1(0.5^n)$, increases with n being the number of linkage groups. If the markers of the present invention resided on two linkage groups, the probability of independent segregation for two subsets of markers is $P(i.s)=0.75$. Out of 397 meiotic products tested from *P. squamulatum*, 298 would have shown independent segregation for two subsets of markers unless a mechanism driving extreme distorted segregation were operating. Therefore, it can be assumed that all 12 nucleic acid markers belong to the same linkage group since any interchromosomal recombination would have significantly altered this tight linkage in a progeny size of 397 individuals.

It is also unlikely that there is saturation of a small region of a linkage group with nucleic acid markers even though a targeting strategy of bulked segregant analysis is used with 16 individuals in each bulk. A similar study on another heterozygous plant using a targeting strategy (four genotypic pools of 14 individuals each) with AFLP markers found 29 out of 3200 AFLP markers displayed linkage to the disease-resistance locus (*Phytophtora infestans* in potato) and eight mapped within the targeted 6cM genetic interval (Meksem et al., Mol. Gen. Genet., Volume 249, 74–81, 1995). Only two of the AFLP markers cosegregated with the trait in a population size of 461 individuals. The population size was designed to allow high-resolution mapping within the 6 cM interval. Given the population size of 397 individuals in the present invention and no verifiable recombination among 12 apomixis-linked markers out of approximately 4,000 total, it is concluded that the gene of the present invention lies in a region of the genome where recombination is repressed, and this region, herein defined as an ASGR, probably contains a disproportionate number of single-dose alleles.

Nothing presently is known of the nucleic acid basis for apomixis. Evidence, from the following examples of a large segregating population, that apospory is controlled by an ASGR is antagonistic with a recently postulated model that the mechanism for apomixis, including apospory, is based on asynchronous expression of many duplicate genes in polyploid angiosperms (Carman, Biol. J. Linn. Soc., Volume 61, 51–94, 1997). Following this hypothesis, it would not have predicted the segregation of a trait with a significant associated region of hemizygosity in the *P. squamulatum* genome. Furthermore, it is noteworthy that this ASGR may be conserved in several other species of Pennisetum where many of the same nucleic acid markers are tightly linked to apospory (Lubbers et al., Theor. Appl. Genet. Volume 89, 636–642, 1994; Roche et al., unpublished). The level of hemizygosity that is observed in the present invention around the apomixis locus suggests that at least a portion of the chromosomal homolog bearing the locus in *P. squamulatum* has been isolated by the lack of recombination for a considerable period of time. The ASGR could be a unique region that underwent extensive sequence divergence as a consequence of its recombinational isolation from the remainder of a progenitor genome, and could have radiated largely intact during hybridization and speciation within the genus.

Solid evidence for the lack of recombination near the apomixis locus has been found in the present invention and to a lesser extent in a preliminary study of diplospory in Tripsacum (Grimanelli et al., 1995; supra). Several mechanisms could be postulated as the genetic basis for non-recombination. I. The apomixis locus could be located in a centromeric or other heterochromatic region of a chromosome. Recombination is known to be reduced in centromeric regions of the genome (Wu et al, 1993, supra; Sherman et al., 1995, supra). The centromeric location of the apomixis locus remains a viable hypothesis, and extreme linkage disequilibrium of surrounding sequences previously observed (Lubbers et al, 1994, supra) would have been promoted by the lack of recombination. II. The apomixis locus could be located in a heterozygous inversion or in a region of DNA introgressed from another species. Inversions can cause localized asynapsis and non-homologous pairing during meiosis, or when paired with homologous segments, form loop bivalents (Schultz-Shaefer, Cytogenetics: Plant, Animal and Human. Springer-Verlag, New York, 1980). A single crossover event in a paracentric inversion can result in dicentric and acentric chromatids which carry genetic duplications and deficiencies, respectively. Pollen grains carrying these aberrant chromatids usually abort and would preclude the recovery of recombinants in this region. III. It is also possible that the ASGR represents a complex locus through which apospory is controlled not by a single gene but rather two or more genes which could be maintained as an intact genetic unit. Mechanisms to prevent recombination within this unit would be required (Charlesworth, Curr. Biol., Volume 4, 739–741, 1994) and might involve those described above. Well documented examples of complex loci in eukaryotes are meiotic drive systems in animals (Lyttle, Annu. Rev. Genet., Volume 25, 511–557, 1991; Trends Genet., Volume 9, 205–210, 1993), the human major histocompatibility complex (Trowsdale, TIG, Volume 9, 117–122, 1993), the Chlamydomonas mating-type locus (Ferris et al., Cell, Volume 76, 1135–1145, 1994) and the self-incompatibility locus in Brassica (Boyes et al., The Plant Cell, Volume 9, 237–247, 1997). Of the characterized systems, several components are shared although the molecular mechanisms may be quite different. Significantly there is no recombination observed between the critical genes within the complex loci, and most systems are characterized by rearrangements of regions of low copy and interspersed repetitive DNA and polymorphisms of chromosome structure such as linked inversions, deletions, duplications and translocations.

The existence of a complex locus also might raise the possibility for the involvement of gene silencing as part of the apomixis mechanism. Silencing of alleles required for normal sexual reproduction could occur through several mechanisms, either transcriptional or post-transcriptional (Matzke et al., Trends Genet., Volume 11, 1–3, 1995; Meyer, Biol. Chem. Hoppe-Seyler, Volume 377, 87–95, 1996). If the apomixis locus were a silencing locus and if the silencing acted in trans, it would explain the dominance of the trait in many species, its incomplete penetrance in facultative apomicts, and its potential for suppression by other loci. Evidence for suppression of the apomixis gene has been observed in C. ciliaris (Taliaferro et al., Crop Sci., Volume 6, 473–476, 1996) and in one of the $F_1$ hybrids of the present invention.

In one type of complex locus, meiotic drive, the homozygous state is correlated with lethality, male sterility, or reduced fertility (Lyttle, Trends Genet., Volume 9, 205–210, 1993); therefore, heterozygosity is selectively maintained. In P. squamulatum, the apomixis linkage block is extremely heterozygous, and some of the apomixis-linked clones of the present invention even appear to be hemizygous, i.e., there is no detectable allele other than the one associated with the apomixis linkage group. As far as is known, homozygous aposporous apomicts do not occur in nature (Nogler, Gametophytic apomixis, In: Embryology of Angiosperms, BM Johri (ed.), Springer-Verlag, 475–518, 1984). If the apomixis allele itself (Nogler, 1984, supra) or an allele held in association by linkage disequilibrium were recessive lethals in haploid gametes (Richards, Apomixis Newsletter, 9–3.htm, 1996), survival of the male gametophyte could only occur if the gamete-lethal gene were compensated for by a normal allele in unreduced gametes. Thus, polyploidy, due to occasional fusion of unreduced male gametes (which would be the only functional male gametes carrying the apomixis trait) with unreduced female gametes, should be a natural outcome and could explain the predominance of polyploidy in apomicts. In addition, if the apomixis locus were actually a strong silencing locus (Matzke et al, 1993, supra; Jorgensen, 1994, supra), the penetrance of the silencing effect might even be enhanced in polyploids (Scheid et al., Proc. Natl. Acad. Sci., Volume 93, 7114–7119, 1996; Guo et al, Genetics, Volume 142, 1349–1355, 1996).

Crucial to the success of map-based cloning is the ability to position the trait phenotype with respect to nucleic acid markers based on recombination distance. In the absence of genetic recombination, physical mapping becomes a tedious, but essential process for ordering nucleic acid markers associated with the trait. Once the gene(s) associated with apomixis is/are isolated, the gene(s) can be inserted into plasmids for increase, maintenance and amplification by known procedures. Several methods are known for attempting the insertion of genes into plant and animal material. These range from pollen transformation techniques (Ohta, PNAS U.S.A., Volume 83, 715–719, 1986; Smith et al, Plant Science, Volume 104, 49–58, 1994; deWet et al, International Patent Application WO 85/01856; all herein incorporated by reference), electroporation techniques (Rhodes et al, Science, Volume 240, 204–207, 1988; Krzyzk, et al., U.S. Pat. No. 5,416,010; both herein incorporated by reference) and microprojectile gene transfer techniques. Some methods utilize polyethylene glycol mediated systems to assimilate the provided gene into a cell line. Basically, each method is designed for implanting selected genes into plant cells (or protoplasts) and incorporating those genes into the genome of the selected species (Kamo et al, Planta, Volume 172, 245–251, 1987). Insofar as apomictic reproduction may be under the control of either expressed or repressed proteins, as yet to be determined, it may be necessary to introduce appropriate regulatory sequences for appropriate control of expression in the host plant.

The microprojectile-mediated gene transfer technique is probably considered the most reliable, effective method and widely-used method in the industry today. Essentially, multiple copies of the gene to be inserted are placed on any of a variety of projectile mediums (tungsten particles, gold particles, etc.) and inserted into a so-called gene gun. Typically by an infusion of air or pressure system, the particles are projected into an explant of plant tissue. Specific systems for identifying the incorporation of the gene into a callus (also called reporter genes) are the E. coil uidA "GUS" gene and the anthocyanin regulatory genes C1 and B. Once transformed cells are identified, they are removed from the callus and transferred to an appropriate growth medium. Eventually through standard tissue culture processes of callus transfer from growth to regeneration media, intact plants are generated. Field studies and progeny testing confirm stable expression of apomictic reproduction and thus incorporation of the appropriate alleles into the genome. Of course other transformation methods could be used as well.

Apomictic reproduction may be under the control of either expressed or repressed proteins. For detecting and identifying these proteins, the protein profile for a non-transformed cell line could be compared with that of a similar non-transformed cell line using methods well known in the art thereby revealing proteins instrumental in apomictic reproduction. Isolation, elution and biochemical analysis could be conducted by conventional means.

The following examples are intended to further illustrate the invention and are not intended to limit the scope as defined by the claims.

EXAMPLE 1

A population for mapping of the apospory trait was produced from a cross of Pennisetum glaucum (induced tetraploid) X P. squamulatum. The apomictic parent, P. squamulatum, is obligate and could only be used as the male parent since chromosomally reduced gametes which would carry potentially recombinant products of meiosis are produced only during male gametogenesis. Inflorescences of pearl millet (an induced tetraploid from 'Tift 8677') were bagged prior to stigma exsertion. Pollen was collected from P. squamulatum (PS26) and dusted onto the stigmas at anthesis. Since pearl millet is protogynous, there is a gap of 2–3 days between the beginning of stigma exsertion and anther exsertion which allows cross-pollination without emasculation.

For mapping purposes, only segregating alleles from heterozygous P. squamulatum that were contributed to the hybrid were considered, and the pearl millet alleles were ignored. Thus, a pseudotestcross strategy was used for genetic mapping as has previously been done with forest species (Grattapaglia et al, In: Proc. Applications of RAPD Technology to Plant Breeding , 37–40, 1992; herein incorporated by reference). The capacity to form aposporous embryo sacs was determined from microscopic examination of 20 cleared ovules per individual (Young et al., Can. J. Bot., Volume 57, 1668–1672, 1972; herein incorporated by reference). Three hundred ninety-seven $F_1$ individuals comprised the mapping population and each individual was categorized as sexual (no evidence of apospory) or aposporous (included both of the following phenotypes: obligate, where only aposporous sacs were observed or facultative, where both aposporous and sexual embryo sacs were observed). Mode of reproduction was confirmed in over 100 $F_1$ individuals by examining progeny produced after pollination of the $F_1$ with pollen from tetraploid pearl millet homozygous for a dominant "red" marker gene (Hanna and Burton, J. Hered., Volume 83, 386–388, 1992; herein incorporated by reference). The presence of a red progeny indicated that syngamy occurred, most probably in meiotically reduced embryo sacs through sexual reproduction. The development of green progeny from the testcross was a strong indication that parthenogenesis of an unreduced egg, and thus apomictic reproduction, had occurred.

Chi square analysis was carried out to test various models for inheritance. To detect linkage between two loci, the numbers within each gamete class (AB, A, B and null) were determined and $x^2 = (a-b-c+d)/(a+b+c+d)$ where a,b,c and d represented the four gamete classes. The recombination fraction was calculated as the frequency of recombinant gametes, $r=(b+c)/(a+b+c+d)$, as described by Wu et al (Theor. Appl. Genet., Volume 83, 294–300, 1992; herein incorporated by reference) for single-dose alleles linked in coupling.

The $F_1$ population segregated for mode of reproduction, apospory vs. sexuality, which indicated that P. squamulatum was heterozygous for the dominant allele. Individuals were designated as aposporous regardless of the frequency of ovules containing aposporous embryo sacs, i.e., facultative and obligate individuals both were scored as aposporous. The entire population segregated for 162 aposporous: 235 sexual phenotypes, a ratio which does not fit the expected 1:1 of a single-dose allele. Chi-square analysis was used to test for tetrasomic inheritance a s well as tetrasomic inheritance with a linked, homozygous-gamete-lethal allele (Table 1). The segregation ratio best fit the model of tetrasomic inheritance with a linked gametic lethality.

Sherwood et al (1994, supra) proposed tetrasomic inheritance of the trait in C. ciliaris and lethality of the homozygous apomixis locus in male gametes as the model that best fit their data.

TABLE I

| Locus | Model for inheritance | Expected + | Expected − | Observed + | Observed − | $x^2$ | $P_{df-1}$ |
|---|---|---|---|---|---|---|---|
| Apomixis | disomic or tetrasomic random chromosome | 198.5 | 198.5 | 162 | 235 | 13.42 | <0.01 |
|  | tetrasomic, random chromatid | 184 | 213 | 162 | 235 | 4.9 | 0.03 |
|  | tetrasomic, random chromatid, gamete lethal | 176 | 221 | 162 | 235 | 2.00 | 0.2 |
| ugt204 | disomic or tetrasomic, random chromosome | 40 | 40 | 29 | 51 | 6.05 | 0.015 |
|  | tetrasomic, random chromatid | 37 | 43 | 29 | 51 | 3.22 | 0.075 |
|  | tetrasomic, random chromatid, gamete lethal | 35.5 | 44.5 | 29 | 51 | 2.14 | 0.14 |

EXAMPLE 2

Nucleic acid markers are either RFLP markers, the UGT 197 marker (Table 2) or RAPD markers (Table 2), the remaining eleven markers. Preparation of primers UGT 197-71$w_{850}$ (primer 1) has been described in U.S. patent application Ser. No. 08/532,050 (Hanna et al; which is herein incorporated by reference in its entirety) now U.S. Pat. No. 5,811,636. Primers 1 and 2 of $A10_{300}$, $A14_{200}$, $C4_{500}$ $O7_{550}$, $P16_{950}$, $Q8_{800}$, $R13_{200}$, $U12_{650}$, $V4_{1600}$, $W10_{600}$ and $X18_{550}$ where derived from cloned and sequenced random amplified polymorphic DNAs (Williams et al, Nucleic Acids Research, Volume 18 (22), 6531–6535, 1990; herein incorporated by reference).

Genomic DNA from $F_1$s of the cross in example 1 was isolated from young leaves according to a method modified from Tai and Tanksley (Plant Mol. Biol. Rep., Volume 8, 297–303, 1990; herein incorporated by reference). Ten grams of frozen tissue was ground to a fine powder with liquid nitrogen then added to approximately 75 ml of extraction buffer containing approximately 100 mM Tris-HC1, pH 8.0; approximately 50 mM EDTA, approximately 500 mM NaCl, about 1.25% SDS and about 0.38% sodium bisulfite added just before use. The homogenate was incubated at approximately 65° C. for about 20–60 minutes and subsequently processed according to the Tai published protocol. Genomic DNA is digested with DraI, HindIII, EcoRI, EcoRV, or BamHI; electrophoresed in an about 0.8% agarose gel in Tris-borate-EDTA buffer and transferred to nylon membranes (Genescreen Plus) by the capillary method of Southern (J. Mol. Biol., Volume 98, 503–517, 1975; herein incorporated by reference). Blots were prehybridized and hybridized according to the manufacturers' instructions using aqueous hybridization solutions at about 65° C. PCR-amplified or gel-purified plasmid inserts were labeled with $^{32}P$ by the random hexamer method. Hybridized blots were washed at a final stringency of 0.1×SCC, about 65° C.

Bulked-segregant analysis (Michelmore et al., Proc. Natl. Acad. Sci., Volume 88, 9828–9832, 1991; herein incorporated by reference) was employed to homogenize the sequence heterozygosity within two pools of DNA except around the apospory locus. Equal amounts of DNA from 16 $F_1$ individuals for each of the two phenotypes, aposporous (A) and sexual (S) were pooled and used as templates for PCR. PCR reaction mixes, approximately 25 μl, contained approximately 10 mM Tris-HCl (about pH 9.0), approximately 50 mM KCl, approximately 1.5 MM MgCl$_2$, approximately 0.1% Triton X-100, approximately 100 μM each of DATP, dCTP, dGTP and dTTp; approximately 0.5 μM of each primer, approximately 25 ng genomic DNA, and approximately 0.05 U Taq DNA polymerase (Promega, Madison, Wis., USA). Cycling was performed on a forced-air thermal cycler (Biotherm) programmed for about 6 cycles of about 15 seconds at about 93° C., about 30 seconds at about 36° C., and about 1 minute at about 72° C.; followed by about 36 cycles of about 15 seconds at about 93° C., about 30 seconds at about 40° C., and 1 minute at about 72° C. Primers were obtained as kits of 20 10-base oligonucleotides each (Operon, USA). After all primers had been screened on A and S genomic DNA pools, a search for additional polymorphisms was initiated by using the same sets of primers but in reactions containing pooled template DNA digested with either AluI, HaeIII, MspI, RsaI or TaqI. The primary effect of predigestion would be to eliminate a band if a restriction site fell between two priming sites.

Twenty-two RAPD fragments were isolated from the apospory pool that were absent from the sexual pool. The approach to identify additional RAPDs using the same primers on digested template DNA was successfully applied and allowed the isolation of 19 of the 22 RAPD markers. The distribution of markers with respect to restriction enzyme tended to favor some enzymes over others. The largest number of markers (8), $A14_{200}$, $O7_{600}$, $Q8_{800}$, $W10_{600}$, $M2_{700}$, $I16_{800}$, $X11_{900}$, and $P17_{400}$, was recovered from MspI-digested DNA; HaeIII-$A10_{300}$, $U12_{650}$, $X19_{950}$ and $Y11_{650}$; and RsaI-$P16_{950}$, $X18_{550}$, $C16_{550}$, $E19_{900}$, $219_{250}$; revealed similar numbers (4 and 5, respectively), and AluI-$I9_{250}$, $M11_{1200}$ and TaqI were the least useful (2 and 0 markers, respectively). Of these 22 markers, 15 (Table 1-all plus $M2_{700}$, $I16_{800}$, $Y11_{650}$, $C16_{550}$) have been cloned and end-sequenced. Sequence-specific primers have allowed 11 (All in Table 1 except ugt 197) out of the 15 to be developed into SCARs (Table 2, FIG. 1).

TABLE 2

Primer pairs and amplification conditions for markers tightly linked with apomixis. Bold letters designate the nucleotides in common with the Operon primer. Marker name consists of the Operon primer designation plus a terminal letter indication whether the RAPD fragment was amplified from digested template (H = Hae III, M = MspI, R = RsaI).

| Marker | primer 1 (5'–3') | primer 2 (5'–3') | Annealing | fragment size(bp) |
|---|---|---|---|---|
| A10H | AAACCTTAATCATGCAACCTCGGA | ATGTCACCCGCCTTCTTTGATGCT | 65 | 300 |
| A14M | TTGATTGAGTTTATTCCTATTTGG | GTGCTGGTACAAGAAGAACTGGTC | 55 | 200 |
| C4 | CCGCATCTACAATAAATCA | GAAATAAAGGCACTGGGA | 54 | 500 |
| O7M | CAGCACTGACATCAACTAGGACGA | AGCACTGACCAACTTTACTGAATC | 63 | 550 |
| P16R | CCAAGCTGCCATATCTCCATGCTC | ATCCGGGACATGCTGTGCGATTTC | 65 | 950 |
| Q8M | GAGCTTGNCCAATCGGGAAA | ATGGTGATGGATCTTTGGAC | 60 | 800 |
| R13 | GGACGACAAGAACAAGAAGGACGA | GAATAGCACCCTCAGACAGCACTC | 65 | 200 |
| U12H | TCACCAGCCAGTTCAACCC | ATTGTTTACATACCATCACCAGAA | 60 | 650 |
| V4 | TCGGATAAGCTGTAGGAGTCT | CACATCCATTNTCTCTTCCAG | 55 | 1600 |
| W10M | CATGTATTTCTCTGTCGTACTTGGTC | AGCCCATAAAACAGCTCCTAAA | 60 | 600 |
| X18R | AGTTGGGAAGAAAGCCGAGTTGT | CAATCTTGGAAGTGCGTCGAAAAT | 60 | 550 |
| ugt197 | GGATGAATAAAACGGTGTTGGGAG | AGAACAACCGCACAAGTGAGAGAA | 62 | 850 |
| -71 W | | | | |

EXAMPLE 3

Each RAPD reaction of example 2 that initially indicated a polymorphism between the A and S pools was repeated on four subsets of each large bulk that contained DNA pooled from only four individuals. Reproducible polymorphic fragments were separated on agarose gels, excised and DNA was purified using GeneClean (Biolol, Vista, Calif., USA). Fragments were cloned into pGEM-T (Promega) or T/A cloning vectors (In Vitrogen, San Diego, Calif., USA). The correct clone was confirmed by hybridizing radiolabeled insert (random primed labeling) with a Southern blot of RAPD fragments amplified from all sub-pools (A and S) and parents (pearl millet and P. squamulatum). Clones were end-sequenced using the fmol DNA kit (Promega) and $^{32}$P-labeled primers. Primers with little internal complementarity and a low probability for dimer formation were designed to each end of the sequence. Where possible, the sequence of the Operon primer was included in a longer (about 18–24 nucleotides) sequence-specific primer (Table 2). Optimal amplification for each Sequence-Characterized Amplified Region (SCAR; Paran et al, Theor. Appl. Genet., Volume 85, 985–993, 1993; herein incorporated by reference) was empirically determined by varying annealing temperature (Table 2) and MgCl$_2$ concentration prior to screening of the entire population of 397 individuals.

Based on screening of the entire mapping population (397 individuals), twelve PCR-based markers-11 SCARS and one sequence-tagged site (ugt197), were always present in 162 aposporous individuals and absent from all 235 sexual individuals. Thus, these markers must belong to the same linkage group and are linked in coupling with the trait. No reproducible markers linked in repulsion were found. Although the twelve nucleic acid markers initially detected polymorphisms between relatively small pooled samples of sexual and apomictic genotypes, it was unexpected that they would define a genomic region with no recombination recorded in a progeny size of 397 individuals. These data were accepted only after extensive resampling of ambiguous individuals for classification of embryo sac development and for DNA analysis. One $F_1$ individual originally was categorized as sexual, but contained all of the apomixis-linked markers. Upon reexamination, this plant was indeed highly sexual with only 7% (6/78) ovules showing aposporous embryo sacs. Some form of altered expression/penetrance of apomixis may be functioning in this individual.

EXAMPLE 4

Approximately 15 μg of DNA prepared as indicated in Example 1, above, was digested overnight with about 50 U DraI enzyme according to the manufacturer's reaction conditions (NEB, Beverly, Mass., USA). Electrophoresis of digested DNA was conducted for about 16 hours in approximately 1% GTG agarose (FMC, Rockland, Me., USA) in about 1× TBE buffer. DNA was transferred to Genescreen Plus nylon membrane (NEN, Boston, Mass., USA) according to the manufacturer's instructions. Insert DNA was generated by PCR amplification from RAPD clones using SCAR-specific primers. These DNA fragments were radiolabeled using a Decaprime II kit following manufacturer's instructions (Ambion, Austin, Tex., USA). Southern blots were prehybridized and hybridized at about 65° C in about 6× SSPE, about 1% SDS and about 50 μg of sheared salmon sperm DNA per ml of solution. Hybridized blots were washed at a final stringency of about 0.1× SSPE with about 0.1% SDS at about 65° C. for about 30 minutes.

Only a single marker, ugt 204, has thus far shown recombination with the trait for apospory. This marker represents a single-dose RFLP that has only been scored in 80 individuals from the mapping population. Although it may be linked, it mapped at a considerable genetic distance from the apospory linkage block ($\chi^2=22.05$, $P_{df-1}<0.01$; recombination fraction=0.2374) and is likely to be at a large physical distance from the remaining markers.

Figure 2:
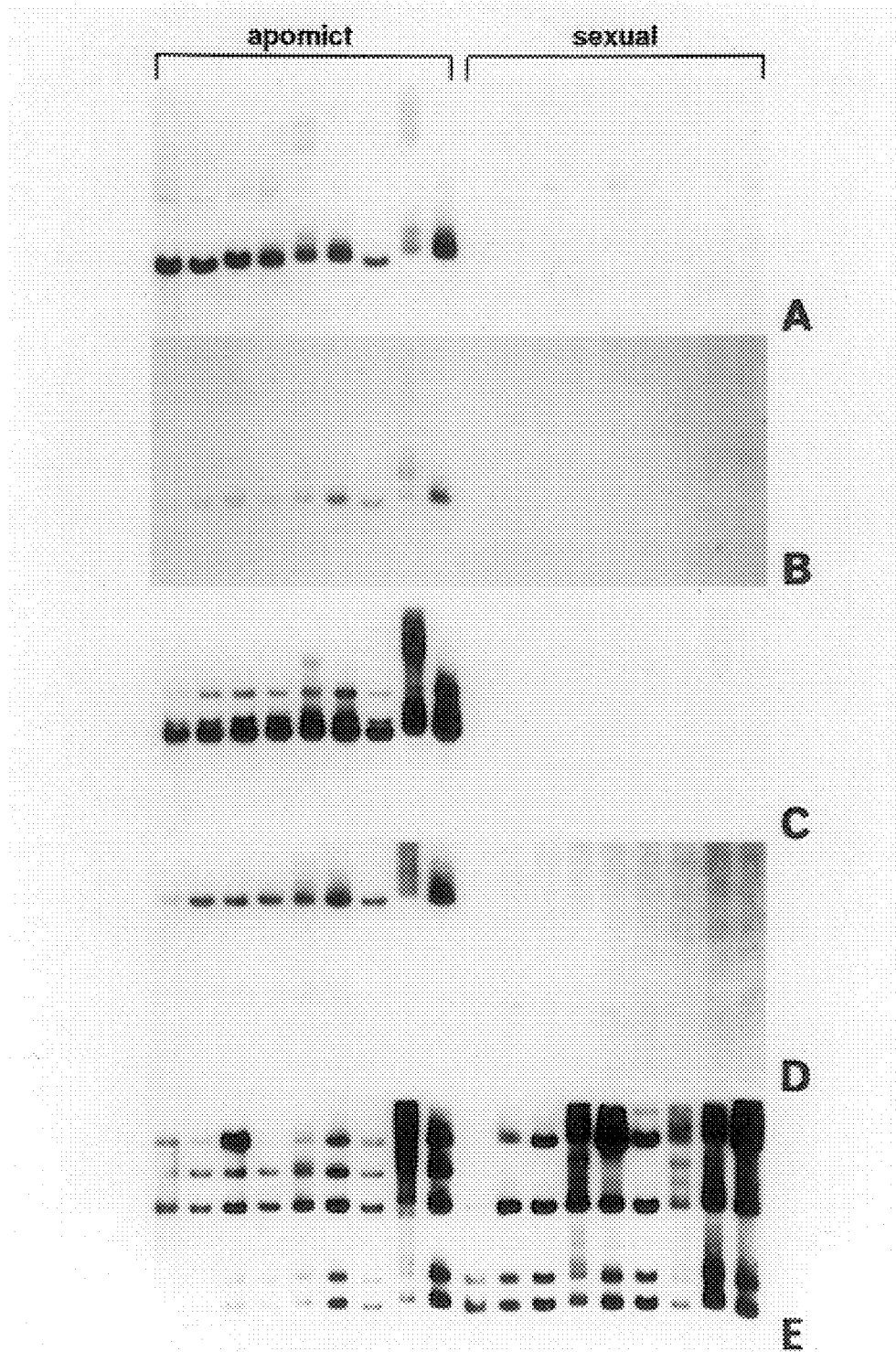
FIG. 2 shows a genomic DNA digest (DraI) of eight apomictic $F_1$ individuals (A) and eight sexual $F_1$ individuals probed with ugt197-71W (A), C4-500 (B) and Q8-800 (C), A14-200 (D) and 07-550 (E). Probes in panels A-D detect hemizygous DNA sequences in the apomictic individuals.

Five out of the eleven cloned RAPD fragments, $C4_{500}$, $Q8_{800}$, $A14_{200}$, $A10_{300}$ and $O_{7600}$; and ugt 197 hybridized as low-copy-number DNAs on genomic Southern blots. When eight sexual and eight apomictic $F_1$ individuals were probed with these six clones, four proved to be hemizygous, i.e., hybridization signal was observed only with the apomictic individuals and not with the sexual individuals (FIG. 2). The remaining single-copy probes were not hemizygous but showed an additional polymorphic fragment in the apomicts that was not represented in the sexuals. Partial hemizygosity near the apomixis locus led to designation of this region as an Apospory-Specific Genomic Region.

The foregoing description is for the purpose of illustration. Such detail is solely for that purpose and those skilled in the art can make variations therein without departing from the spirit and scope of the invention.

We claim:

1. A nucleic acid marker for an apospory-specific genomic region which is
   (a) isolated from genomic DNA of an $F_1$ interspecific hybrid between *Pennisetum squamulatum* and *P. glaucum*; and
   (b) a DNA sequence having a length of about 259 bases, and having a sequence of SEQ ID No. 3.

2. A nucleic acid marker for an apospory-specific genomic region which is
   (a) isolated from genomic DNA of an $F_1$ interspecific hybrid between *Pennisetum squamulatum* and *P. glaucum*; and
   (b) a DNA sequence having a length of about 523 bases, and having a sequence of SEQ ID No.4.

3. A nucleic acid marker for an apospory-specific genomic region which is
   (a) isolated from genomic DNA of an $F_1$ interspecific hybrid between *Pennisetum squamulatum* and *P. glaucum*; and
   (b) a DNA sequence having a sequence of SEQ ID No. 11.

4. A nucleic acid marker for an apospory-specific genomic region which is
   (a) isolated from genomic DNA of an $F_1$ interspecific hybrid between *Pennisetum squamulatum* and *P. glaucum*; and
   (b) contained in *E. coil* wherein said *E. coli* containing said marker is designated by ATCC accession No. 98602.

5. A nucleic acid marker for an apospory-specific genomic region which is
   (a) isolated from genomic DNA of an $F_1$ interspecific hybrid between *Pennisetum squamulatum* and *P. glaucum*; and
   (b) contained in *E. coil* wherein said *E. coli* containing said marker is designated by ATCC accession No. 98601.

6. A nucleic acid marker for an apospory-specific genomic region which is
   (a) isolated from genomic DNA of an $F_1$ interspecific hybrid between *Pennisetum squamulatum* and *P. glaucum*; and
   (b) contained in *E. coli* wherein said *E. coli* containing said marker is designated by ATCC accession No. 98608.

7. A nucleic acid marker for an apospory-specific genomic region which is
   (a) isolated from genomic DNA of an $F_1$ interspecific hybrid between *Pennisetum squamulatum* and *P. glaucum*; and
   (b) contained in *E. coli* wherein said *E. coli* containing said marker is designated by ATCC accession No. 98605.

8. A nucleic acid marker for an apospory-specific genomic region which is
   (a) isolated from genomic DNA of an $F_1$ interspecific hybrid between *Pennisetum squamulatum* and *P. glaucum*; and (b) contained in *E. coli* wherein said *E. coli* containing said marker is designated by ATCC accession No. 98611.

9. A nucleic acid marker for an apospory-specific genomic region which is
   (a) isolated from genomic DNA of an $F_1$ interspecific hybrid between *Pennisetum squamulatum* and *P. glaucum*; and
   (b) contained in *E. coli* wherein said *E. coli* containing said marker is designated by ATCC accession No. 98603.

10. A nucleic acid marker for an apospory-specific genomic region which is
    (a) isolated from genomic DNA of an $F_1$ interspecific hybrid between *Pennisetum squamulaturn* and *P. glaucum*; and
    (b) contained in *E. coli* wherein said *E. coli* containing said marker is designated by ATCC accession No. 98612.

11. A nucleic acid marker for an apospory-specific genomic region which is
    (a) isolated from genomic DNA of an $F_1$ interspecific hybrid between *Pennisetum squamulatum* and *P. glaucum*; and
    (b) contained in *E. coli* wherein said *E. coli* containing said marker is designated by ATCC accession No. 98607.

* * * * *